(12) United States Patent
Merchant (10) Patent No.: US 9,895,489 B2
(45) Date of Patent: Feb. 20, 2018

(54) ANGLED RETRACTABLE NEEDLE

(71) Applicant: Michael Merchant, Franklin, MA (US)

(72) Inventor: Michael Merchant, Franklin, MA (US)

( * ) Notice: Subject to any disclaimer, the term of this patent is extended or adjusted under 35 U.S.C. 154(b) by 45 days.

(21) Appl. No.: 14/841,963

(22) Filed: Sep. 1, 2015

(65) Prior Publication Data

US 2017/0056586 A1    Mar. 2, 2017

(51) Int. Cl.
| A61M 5/34 | (2006.01) |
| A61M 5/158 | (2006.01) |
| A61M 5/162 | (2006.01) |
| A61M 5/32 | (2006.01) |

(52) U.S. Cl.
CPC .......... *A61M 5/1626* (2013.01); *A61M 5/158* (2013.01); *A61M 5/3243* (2013.01); *A61M 5/34* (2013.01); *A61M 2005/1585* (2013.01); *A61M 2005/1586* (2013.01); *A61M 2005/3247* (2013.01); *A61M 2005/3249* (2013.01); *A61M 2005/341* (2013.01); *A61M 2005/342* (2013.01)

(58) Field of Classification Search
CPC ...... A61M 5/1626; A61M 5/158; A61M 5/34; A61M 5/3243; A61M 2005/1585; A61M 2005/341; A61M 2005/342; A61M 2005/3247; A61M 2005/3249
See application file for complete search history.

(56) References Cited

U.S. PATENT DOCUMENTS

| 6,572,586 B1 * | 6/2003 | Wojcik ................. A61M 5/158 |
| | | 128/DIG. 6 |
| 7,413,560 B2 | 8/2008 | Chong et al. |
| 8,221,352 B2 | 7/2012 | Merchant |

* cited by examiner

*Primary Examiner* — Nathan R Price
*Assistant Examiner* — Courtney Fredrickson
(74) *Attorney, Agent, or Firm* — Chapin IP Law, LLC (57) ABSTRACT

A disposable safety needle assembly and safety enclosure for internally shielding a used or contaminated needle includes a needle assembly having a needle cannula slidably disposed within a safety enclosure. An angular orientation to the needle within the enclosure maintains an insertion angle allowing the safety enclosure to remain substantially flush with a dermal surface during and while the needle is inserted. The safety enclosure also includes an internally disposed flexible safety member. The flexible safety member has face portion transversely situated and having a safety feature disposed to the needle and that slides thereon. Retracting the needle within the safety enclosure to a point wherein the sharp tip of the needle is beyond the needle protection section of the flexible member causes the protection section to travel transversely to the direction of motion of the needle. As a result, the safety feature receives the sharp tip of the needle.

19 Claims, 8 Drawing Sheets

ANGLED RETRACTABLE NEEDLE

BACKGROUND

Fluid collection sets, catheters, and intravenous infusion sets are typically used to collect bodily fluids from a patient or to infuse liquids into a patient. These devices typically include a length of flexible plastic tubing with a proximal end connected to a plastic fitting and a distal end connected to a needle, or in the case of a catheter, a tubular assembly. In practice, fluid is transferred via the plastic tubing either to or from the needle or tubular assembly.

Accidental sticks with a needle cannula can be not only painful but can also transmit disease from a patient to medical personnel. Similarly, catheters may retain fluids when they are removed from a patient and transmit disease via these fluids if passed to medical personnel. As a result, nearly all needle assemblies and other sharp medical implements are employed with an apparatus for enclosing the sharp tip of the needle or tubular assembly both prior to and after use.

SUMMARY

A needle insertion apparatus includes a safety enclosure having a needle assembly slideably disposed therein, in which the needle assembly having a use position and a safe position to prevent accidental needle insertion. The needle assembly includes a pointed tip, elongated shaft, a tubular receptacle and a cannulated interior for fluidic communication from the needle tip to a fluid conduit attached to the tubular receptacle, and the safety enclosure is adapted to enclose the needle in response to displacement of the needle assembly to the safe position within the safety enclosure. An angular support disposing the needle assembly at an angular orientation relative to a base of the safety enclosure, in which the base defining a working position of the needle for communication with a patient dermal surface (i.e. on top of the skin surface). The angular orientation disposes the needle assembly at a downward angle toward the skin such that the pointed tip is closer to the base than the tubular receptacle. The downwardly angled needle tip extending below a plane defined by the base when the needle assembly is in the use position, avoiding a tendency for the needle to pull upwards from a pivoting movement about the base if pressure is applied to the rear of the enclosure at the tubular receptacle.

In a particular configuration, the needle can be a fistula needle, typically used for dialysis, and which has a larger diameter to accommodate increased blood flow required for dialysis treatment. The needle may also be a more general blood drawing needle for drawing blood from a patient.

In addition to hazards presented by an open needle, configurations herein are based, in part, on the observation that the safety enclosure used to encapsulate the needle raises the needle off the dermal surface. Unfortunately, conventional approaches that utilize a safety enclosure at the needle hub suffer from the shortcoming that this elevation causes the safety enclosure to bias at an angle when the needle is inserted, causing a pivoting orientation on a forward corner of the safety enclosure. Such pivoting can result in an upward lateral force on the needle, tending to force the needle up toward the dermal surface, interfering with optimal blood flow, increasing the chance of discomfort and possible tissue damage if sufficient downward "pivotal" force occurs at the opposed tubular end of the structure. Accordingly, configurations herein substantially overcome the above-described shortcomings by providing a safety enclosure having angular needle orientation for disposing the needle in an angular downward position with respect to a base of the safety enclosure, allowing the needle extending from the safety enclosure to penetrate the skin while allowing the base to remain flush or substantially flush on the dermal surface for mitigating and upward pivotal force.

During needle usage, operator (i.e. nurse or medical technician) protection prior to use is typically achieved by a rigid plastic tube that surrounds a portion of the needle including the sharp edge. This rigid tube typically has a proximal end frictionally mounted to or near the hub and a distal end that extends beyond the distal end of the piercing element. The rigid tube itself surrounds the needle and prevents contact with the needle point until it is removed. Once removed, the plastic tube is discarded immediately prior to use of the piercing element.

One prior art form of protecting the needle after use is the use of a tubular shield that can be telescoped relative to both the hub and piercing element from a proximal position where the piercing element is exposed to a distal position where the piercing element is safely within the tubular shield. Shields of this type typically include means for releasably holding the shield in its proximal position and for holding the shield more securely in its distal position. Some devices include a spring for generating relative movement between the shield and the piercing element. In some instances the piercing element is withdrawn proximally into the shield.

However, this prior art method requires movement of the hands of the medical provider toward the exposed needle and therefore may allow needle stick injuries during the recapping.

In addition, a small volume of blood or other bodily fluid may remain in or on a piercing element after the piercing element has been withdrawn from the patient or when a catheter is removed from a patient. This residual fluid may splatter as the piercing element is retracted rearward into the prior art shield. In general, the larger the bore of the needle, the larger the acceleration of the needle in the proximal direction, and any transverse acceleration may result in the splatter of the residual bodily fluid.

The prior art has worked to reduce the likelihood of such splatter. In one example, an indwelling injector needle assembly has the hub slide along an inner periphery of the holder between a first position near the distal end of the holder and a second position near a proximal end of the holder. The latching mechanism is formed in and disposed between the hub and the holder so that the hub is inhibited from moving from the first position toward the second position, and vice versa. The needle edge can be retracted within the holder while remaining fixed to a patient's skin.

However, this form of the prior art has at least one problem. This structure includes a non-rotating needle. As is known in the art, a rotatable needle is preferable to a non-rotatable needle in order to maximize blood or fluid flow to or from a vessel in which the needle is inserted. The prior art device prevents the needle from being rotated after cannulation. The needle and hub cannot rotate relative to the cylindrical holder due to the lug being slidably engaged with the guide groove in the hub. Therefore the needle cannot be rotated when needed after cannulation in order to maximize blood or fluid flow to or from the vessel.

Another prior art device describes a system which provides a snap-on exterior mounted enclosing guard can be added to a needle assembly. A spring forms an essential element of this safety needle assembly. In particular, the spring includes an turned in flange which is described as imperforate, such that it acts as a blocking flange. The enclosing guard, by way of the imperforate blocking flange, upon the withdrawal of the needle from the blood donor or patient, blocks the contaminated needle point.

Thus, this prior art device is limited in its use of materials and design in that the flange must be imperforate in order to prevent the needle tip from coming into contact with any worker. However, the enclosing guard is in proximate relation to and actually touches the needle cannula while it is being withdrawn from the patient. Thus, this assembly can become contaminated itself. Although the needle point is blocked, the system may still contaminate the worker by the blood or fluid which is on the enclosing guard.

Thus, what is needed is a safety needle device that allows for the maximum blood or fluid flow to or from the vessel, and overcomes the limitations of the prior art. The present invention addressed the problem of potential worker contamination both by needle stick and accidental exposure without needle stick. A new system and enclosure means is provided which prevents the needle from exiting the enclosure once it has been withdrawn from the patient, shields the needle point and simultaneously isolates the locking member from contact with the worker and any other patient or person in proximity to the patient. In addition, the system and enclosure of the present invention also prevents the medical care giver from accidentally coming in contact with body fluid of the patient.

The needle assembly has a needle cannula which is longitudinally disposed within a safety enclosure and slidably maintained therein. The safety enclosure incorporates an internally disposed flexible member situated along the longitudinal plane, having a needle protection section transversely disposed to the needle cannula and cooperatively sliding thereon. The needle protection section can either be imperforate, in which case a detent is advantageously disposed thereof to capture the tip of the needle cannula, or it can be perforate, in which case the perforation is of a diameter less than the diameter of the cannula such that it can capture and retain the tip of the cannula. Retraction of the needle cannula within the safety enclosure to a point wherein the sharp tip of the needle cannula is beyond the needle protection section of the flexible member causes the protection section to travel transversely to the direction of motion of the needle cannula and block the sharp tip from exiting the enclosure, thereby maintaining the needle safely after use and preventing the accidental exposure with the patient's body fluids.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The following detailed description sets forth numerous specific details to provide a thorough understanding of the invention. However, those skilled in the art will appreciate that the invention may be practiced without these specific details. In other instances, well-known methods, procedures, components, protocols, processes, and circuits have not been describe in detail so as not to obscure the invention.

Certain terminology may be used in the following description for convenience only and is not limiting. The words "lower" and "upper" and "top" and "bottom" designate directions only and are used in conjunction with such drawings as may be included to fully describe the invention. The terminology includes the above words specifically mentioned, derivatives thereof and words of similar import.

Where a term is provided in the singular, the inventors also contemplate aspects of the invention described by the plural of that term. As used in this specification and in any claims, the singular forms "a", "an", and "the" include plural references unless the context clearly dictates otherwise, e.g. "a derivative work". Thus, for example, a reference to "a method" includes one or more methods, and/or steps of the type described therein and/or which will become apparent to those persons skilled in the art upon reading this disclosure.

Unless defined otherwise, all technical, legal, copyright related and scientific terms used herein have the same meaning or meanings as commonly understood by one of ordinary skill in the art to which this invention belongs. Although any methods and materials similar or equivalent to those described herein can be used in the practice or testing of the present invention, the preferred methods, constructs and materials are described herein. All publications mentioned herein, whether in the text or by way of numerical designation, are incorporated herein by reference in their entirety. Where there are discrepancies in terms and definitions used by reference, the terms used in this application shall have the definitions given herein.

The term "variation" of an invention includes any embodiment of the invention, unless expressly specified otherwise. A reference to "another embodiment" in describing an embodiment does not necessarily imply that the referenced embodiment is mutually exclusive with another embodiment (e.g., an embodiment described before the referenced embodiment), unless expressly specified otherwise.

The terms "include", "includes", "including", "comprising" and variations thereof mean "including but not limited to", unless expressly specified otherwise. The term "consisting of" and variations thereof includes "including and limited to", unless expressly specified otherwise.

The terms "a", "an" and "the" mean "one or more", unless expressly specified otherwise. The term "plurality" means "two or more", unless expressly specified otherwise. The term "herein" means "in this patent application, including anything which may be incorporated by reference", unless expressly specified otherwise. The phrase "at least one of", when such phrase modifies a plurality of things (such as an enumerated list of things) means any combination of one or more of those things, unless expressly specified otherwise.

The phrase "based on" does not mean "based only on", unless expressly specified otherwise. In other words, the phrase "based on" describes both "based only on" and "based at least on". The term "represent" and like terms are not exclusive, unless expressly specified otherwise.

The term "whereby" is used herein only to precede a clause or other set of words that express only the intended result, objective or consequence of something that is previously and explicitly recited. Thus, when the term "whereby" is used in a claim, the clause or other words that the term "whereby" modifies do not establish specific further limitations of the claim or otherwise restricts the meaning or scope of the claim.

The terms "such as", and/or "e.g." and like terms means "for example", and thus does not limit the term or phrase it explains.

The term "determining" and grammatical variants thereof (e.g., to determine a price, determining a value, determine an object which meets a certain criterion) is used in an extremely broad sense. The term "determining" encompasses a wide variety of actions and therefore "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing, and the like. It does not imply certainty or absolute precision, and does not imply that mathematical processing, numerical methods or an algorithm process be used. Therefore "determining" can include estimating, predicting, guessing and the like.

In the embodiments that follow, the safety needle assembly has a needle cannula that is slidably disposed within a safety enclosure. The safety enclosure incorporates an internal safety cover situated along the longitudinal axis of the needle cannula, having a needle protection face section transversely disposed to the needle cannula. The needle protection face section can either be imperforate, in which case a detent is disposed thereon to capture the tip of the needle cannula, or it can be perforate, in which case the perforation through the protection face has a diameter less than the diameter of the needle cannula. In this way, the needle cannula is captured and retained within the safety enclosure.

Figure 1:
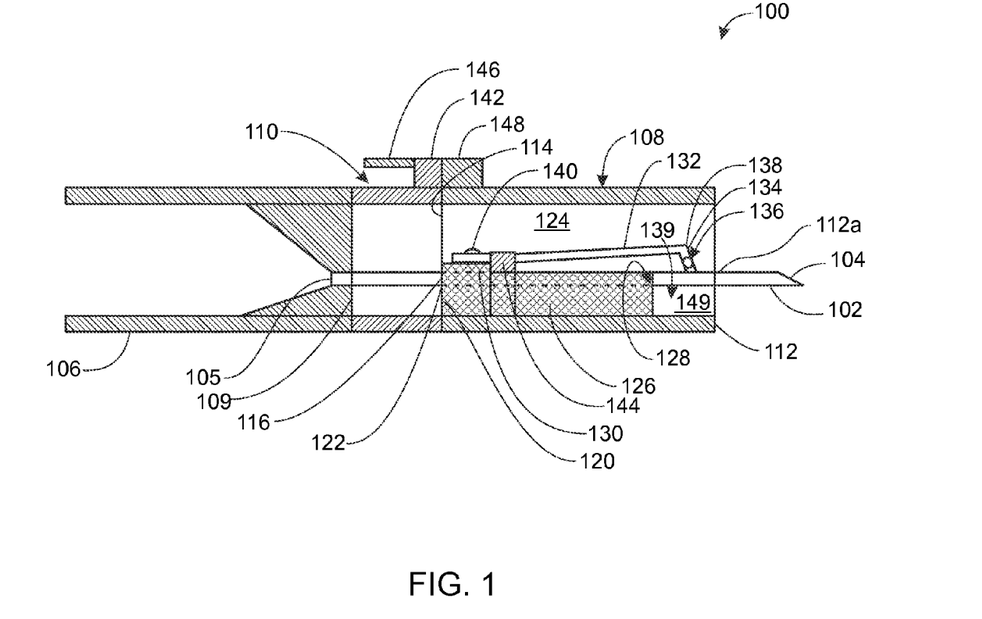
FIG. 1 is a cross sectional view incorporating an embodiment of the present invention in a use position.
Figure 2:
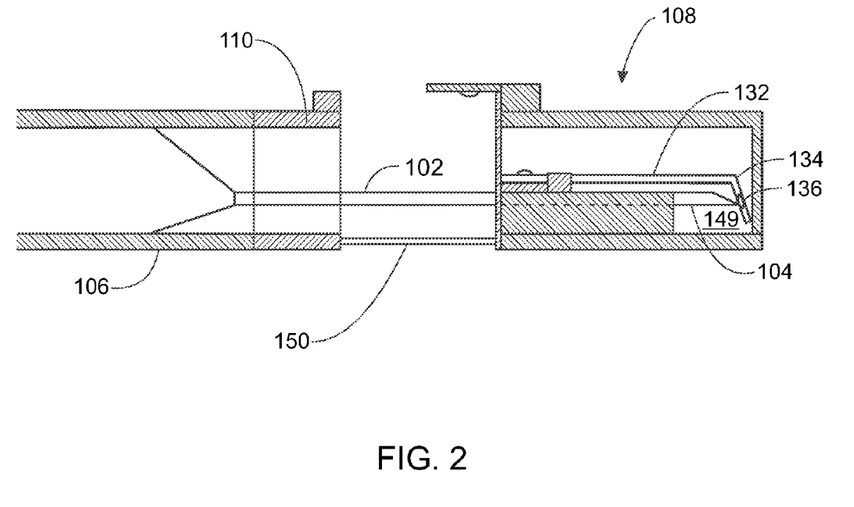
FIG. 2 is a cross sectional view incorporating an embodiment of the present invention the safety position.

With respect to FIGS. 1 and 2, a safety needle assembly 100 is provided that includes a needle cannula 102 suitable for the insertion or removal of fluids to or from a patient. The needle cannula 102 includes a tapered point 104 and a proximal end 105. The proximal end 105 of the needle cannula 102 is attached to a piece of flexible tubing 106 via a connector 109 or through the use of a bonding material as is known in the art.

A safety enclosure 108 includes a forward face 112 having an orifice 112*a* and a distal end 114 and orifice 116 as well. The orifices 112*a* and 116 are both sized and configured to allow the tapered point 104 and the body of the needle cannula 102 to slidably pass therethrough. A base portion (hub, hub portion) 110 of the safety needle assembly is secured to the flexible tubing 106. The base portion (hub, hub portion) 110 includes a front face 120 and an orifice 122. Orifice 122 is also sized and configured to allow the body of the needle cannula 102 to pass slidably therethrough.

The safety enclosure 108 includes an interior portion 124 that includes a base portion 126 that extends a portion of the longitudinal length of the safety enclosure 108, but does not extend the entire length. The base portion 126 includes a glide canal 128 into which the needle cannula 102 is disposed within. Thus, the needle cannula 102 is slidably and securely disposed within the safety enclosure 108.

Disposed within the interior portion 124 of the safety enclosure 108 is a first base portion 130 on which a flexible safety cover 132 is disposed. As will be discussed in more detail below, the flexible safety cover 132 includes a face portion 134 that includes a safety feature 136 and in which the face portion 134 is disposed in a generally downward direction by bend 138. The safety cover 132 is biased in a generally downward direction such that so long as the needle cannula 102 is touching the safety cover front face 134, the safety cover 132 will not move. When the needle cannula 102 is moved such that it is no longer touching the front face 134, the safety cover 132 and front face 134 will move in the downward direction shown by arrow 139 and depicted in FIG. 1.

Figure 3:
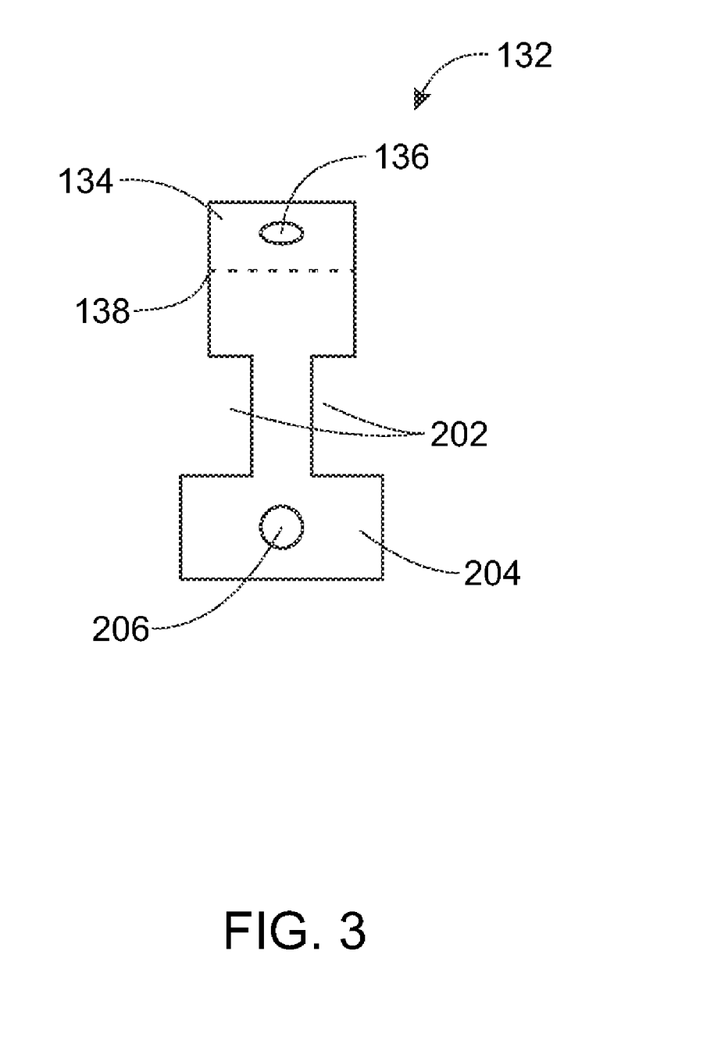
FIG. 3 is top view of the flexible safety member according to an embodiment of the invention located.

The safety cover 132 is depicted in FIG. 3 includes the front face 134, safety feature 136, and first bend 138. In addition, the safety cover 132 further includes notch 202 and rear portion 204. With reference again to FIGS. 1 and 2, the interior portion 124 further includes a second base portion 144. The second base portion 144 is sized and configured to be disposed within notch 202. In this way, movement of the safety cover separate and distinct from the safety enclosure 108 is prevented. The safety cover 132 is affixed to the first base portion 130 via the cooperating post 140 and hole 206.

Figure 4:
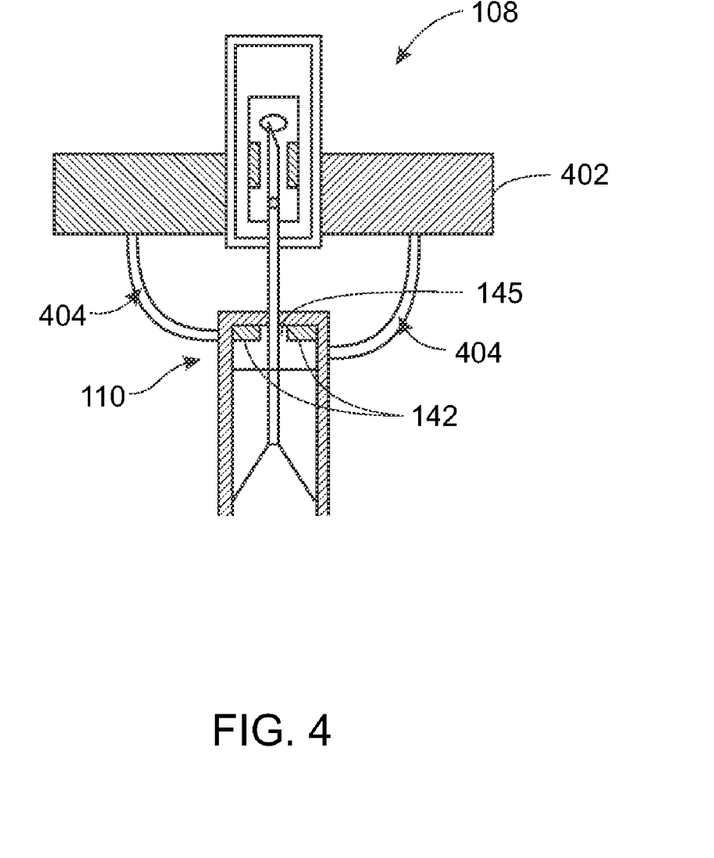
FIG. 4 is a top view of an apparatus incorporating an embodiment of the present invention.

As depicted in FIG. 1, the needle cannula is shown in its extended configuration in which it is to be used to insert or remove fluids from a patient. In this configuration, the safety enclosure 108 is removably secured to the base portion (hub, hub portion) 110 via a hooking mechanism described below. As depicted in FIGS. 1, 2, and 4 the base portion (hub, hub portion) 110 includes a pair of posts 142 having a notch 145 disposed therebetween. The safety enclosure 108 includes a hook portion 146 (or latch 146) that extends longitudinally from the top surface 148 of the safety enclosure 108 that is sized and configured to cooperate with posts 142 and notch 145 to securely and yet removably secure the safety enclosure 108 to base portion (hub, hub portion) 110. The hook portion 146 latches with the notch 145 to prevent any motion of safety enclosure 108, thus preventing the accidental uncovering of the needle cannula 102. The hook portion 146 is also sized and configured to allow a medical care giver to use the present invention in a one-handed operation. By unlatching the hook 146 and sliding the safety enclosure to cover the needle tip (tapered point) 104 using the same hand, the danger of accidently contacting the needle tip 104 is greatly reduced.

In the configuration depicted in FIG. 1, the needle cannula 102 is preventing the downward motion of the front face 134. In this configuration, the needle cannula 102 is extended beyond the front face 134 of the safety enclosure 108 and is ready for use. As can be seen, interior area 149 within the safety enclosure 108 is sized and configured to receive the front face 134 of the safety cover 132.

As depicted in FIGS. 2 and 4, the needle cannula 102 has been withdrawn into the safety enclosure 108 and the safety cover 132 is now free to move laterally such that the front face 134 is disposed in front of the tapered point 104. In addition, the hub portion (base portion, hub) 110 and safety enclosure 108 are prevented from moving beyond a suitable length by flexible member 150 that is attached to both the hub (hub portion, base portion) 110 and safety enclosure 108. Flexible member 150 is also known as flexible coupling 150 or extensible retainer 150. In addition, as depicted in FIG. 4, flexible wings 402 may be attached to the safety enclosure 108 to allow easier use by medical personnel that may bend the wings 402 upward to facilitate grasping the safety enclosure 108 and then used to provided a surface for taping the safety enclosure 108 to a patient's skin to secure the needle cannula 102 within the patient. In addition, to prevent the safety enclosure 108 from traveling too far and sliding off the end of the needle tip 104, a pair of flexible tethers 404 may be coupled to the base portion (hub, hub portion) 110 and the safety enclosure 108 or the flexible wings 402. These flexible tethers 404 comprise the flexible coupling. Particular configurations include at least one tether between the safety enclosure and the tubular receptacle or flexible wing 402 configured to limit travel of the tubular receptacle for preventing complete withdrawal of the needle 102 from the safety enclosure 108. An example configuration employs a pair of tethers on opposed sides of the tubular receptacle, although any suitable number of tethers or other restraint may be employed for preventing complete withdrawal of the needle from the safety enclosure.

Figure 5:
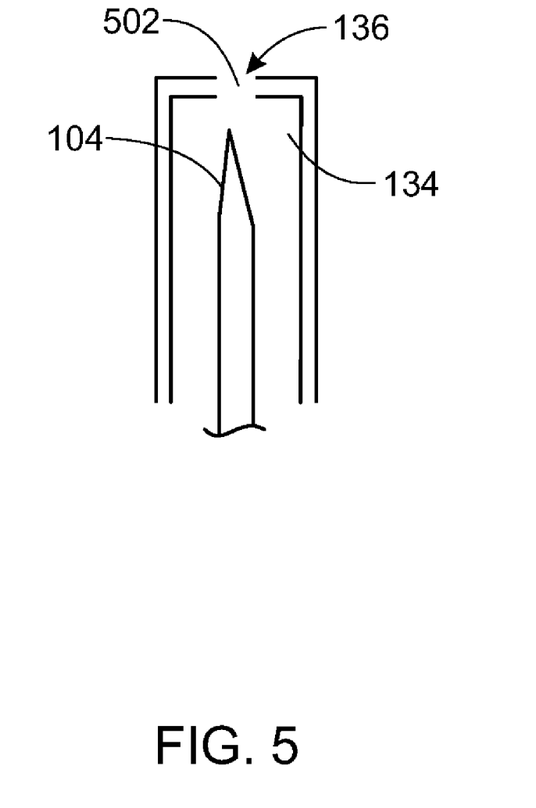
FIG. 5 is cross sectional view of a first embodiment of the safety feature of the present invention.
Figure 6:
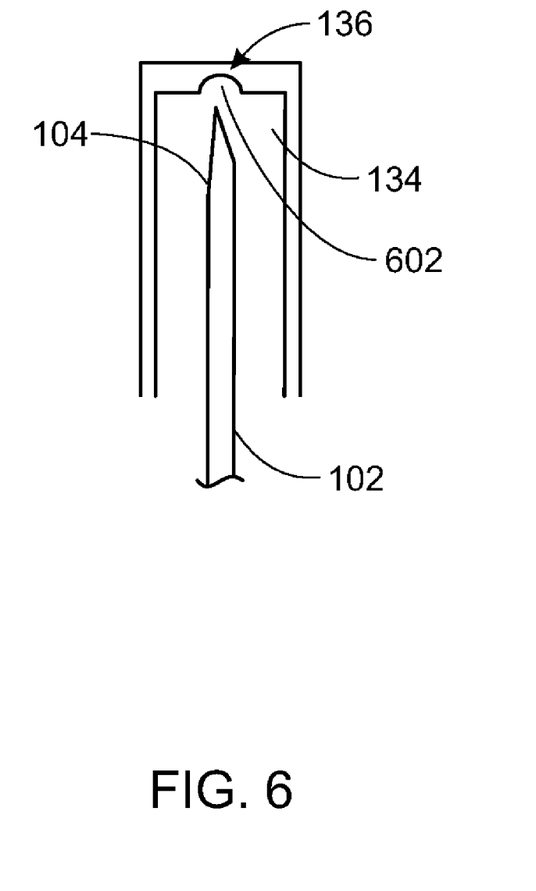
FIG. 6 is a cross sectional view of a second embodiment of the safety feature of the present invention.

As further shown in FIGS. 5 and 6, the tapered point 104 is received in the safety feature 136. In one embodiment, the safety cover 132 is imperforate and the front face 134 includes a detent 602 that is sized configured to receive the tapered point 104 of needle cannula 102 and prevent its movement within the safety enclosure 108. In another embodiment, the safety cover 132 is perforate and front face 134 includes an orifice 502 that is sized and configured to receive only the tip of the tapered point 104 and thereby prevents movement of the needle cannula 102 within the safety enclosure 108. In either embodiment, since the safety cover 132 is internal to the safety housing 108, any fluid which contacts it while it is traveling along the length of the cannula will be maintained within the enclosure.

Once enclosed, the practitioner and others are shielded from any accidental stabs from the tapered point 104. Similarly, since the safety cover 132 is internal to the safety enclosure 108, any fluid which contacts it while it is traveling along the length of the needle cannula 102 will be maintained within the safety enclosure 108. However, this shielding function would be frustrated if the proximal end of the safety enclosure 108 was capable of moving distally beyond the distal end of the needle cannula 102, i.e., past the sharp point. The extensible retainer 150 connects the safety enclosure 108 to the hub 110. As the safety enclosure 108 moves distally along the needle cannula 102, the extensible retainer 150 extends up to, but not beyond, a predetermined length. The extensible retainer 150 thus provides an extensible length beyond which the safety enclosure 108 may not distally extend.

The needle cannula 102 may be any form of needle cannula suitable for a particular usage. For example, the needle cannula 102 may be a Quincke type spinal needle having a gauge in the range from about 12 to 27 and in lengths from about 1" to 7", or the needle cannula 102 may be a Whitacre type spinal having a gauge from about 22 to 27 lengths from about 3½" to 5". Of course, other types of spinal needles could be used. The needle cannula 102 may also be an epidural needle having a gauge of about 17 to 22 and 2 to 3 inches in length. The needle cannula 102 may also be a fistula needle for dialysis or a blood drawing needle in a blood drawing device as well. These needle cannulas 102 are exemplary only, and it will be understood that the present invention is not limited to a particular needle gauge, type or length.

As discussed above, the needle cannula 102 has a proximal end 105 fixed to the base portion (hub, hub portion) 110, and a distal end that terminates at a sharp tapered point 104. It will be appreciated that the distal end does not necessarily have to terminate at a sharp tapered point 104, and the distal end may have a blunt tip, for instance for use in catheters. The base portion (hub, hub portion) 110 may be any suitable device known in the art, and may have flanges adapted to mate with a locking luer collar, for example. Other types of base portion (hub, hub portion) 110 are possible, such as providing a screw cap adapted to screw onto a corresponding male member of a medical device, which may be a syringe, catheter, etc. Alternatively, the base portion (hub, hub portion) 110 may be the base of a syringe to which the needle assembly is permanently attached. Any method known in the art may be used to fix the hub (hub portion, base portion) onto the proximal end of the cannula, such as adhesives, welding, mechanical engagement or the like.

The safety housing 108 may be sized and configured for various usages. For example, the safety cover 108 may be substantially rectangular in shape, and made of plastic, metal or any other sufficiently tough material that can resist puncturing by the point of the cannula. The safety housing 108 has an outer surface, which may be either smooth or provided with a roughened surface to provide a gripping surface for the user. The housing also may have a down-clip member that may be used to permit gripping and placement of the system by the user. In particular, the down-clip member may be employed to effectuate such action rather than using the wings or flanges, which may not provide the same positive gripping surface and control as use of the down-clip member.

In addition, although the outer surface of the safety housing 108 is preferentially solid, it will be appreciated that the outer surface may also have openings, such as holes, slits, or the like to reduce on material costs, but that any such opening should not permit access to the bodily fluid or permit escape of that fluid. For purposes of this disclosure, such a configuration is still considered to cover that portion of the cannula over which such the safety housing 108 is disposed.

Figure 7:
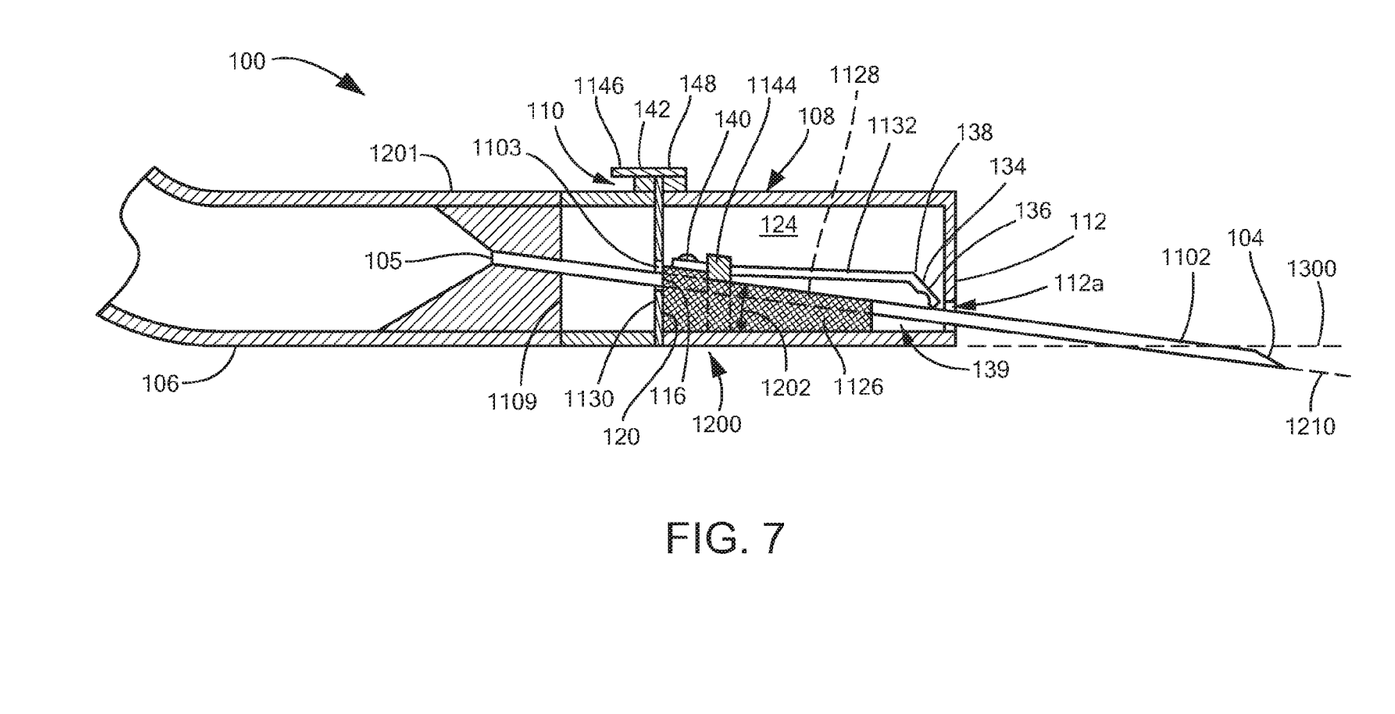
FIG. 7 shows a side view of an angled needle in a use (deployed) position.

FIG. 7 shows a side view of an angled needle in a use (deployed) position. Referring to FIGS. 1 and 7, the angled needle 1102 follows an angled or diagonal path through the interior portion 124 of the enclosure 108 at an angle 1202 relative to a bottom surface 1200, or base. A base portion 1126 angles downward toward the forward face 112 such that the angled needle 1102 is only slightly above the bottom surface 1200 upon emerging from the forward face 112 through an orifice 112a. An angled second base portion 1144 likewise secures the safety cover 132 substantially parallel and biased toward the angled needle 1102 such that the front face 134 will angle downward to dispose the safety feature (aperture or dimple) 136 in the path of the angled needle once retracted. The angled needle 1102 follows path such that the angle 1202 is intended to dispose the point 104 of the needle into the dermal surface of a patient while the bottom surface 1200 remains flush or substantially flush with the dermal surface.

The angled second base portion 1144 therefore defines an angular support including an elevated base angling downward toward a forward end at the forward face 112 of the safety enclosure 108, such that the forward end is defined by a side of the enclosure 108 nearest the pointed tip or point 104. The base, or bottom surface 1200, has a thickness defining a height from which the needle tip or point 104 emerges from the safety enclosure 108, such that the needle assembly is adapted for slideable insertion into a patient dermal surface supporting the safety enclosure 108.

The base defined by the bottom surface 1200 is adapted for resting substantially flush on the patient dermal surface, and the needle tip 104 is adapted to extend along an insertion path 1210 below the patient dermal surface in the use position, such that the base prevents an upward pivotal movement of the needle tip. The downward angle 1202 of the needle 1102 causes it to extend below the dermal surface when sufficiently extended, such that the base 1200 can remain flush or substantially flush and still permit the needle point 104 to breach the dermal surface 1300. The flush or near flush disposition of the base 1200 prevents a pivot motion causing the base 1200 to act as a fulcrum tending to pull the needle 1102 up and out of the patient dermal surface from rearward pressure at a tubing side of the enclosure 108.

In the configuration shown, the safety enclosure 108 is elongated along the length substantially parallel to the elongated shaft, in which the needle assembly is secured in the hub 110 for defining a tubular receptacle 1201 slideable along the length of the safety enclosure 108 for retracting the pointed tip 104 inside the safety enclosure 108 as the tubular receptacle 1201 is drawn away from the safety enclosure 108.

To accommodate the angle 1202, a connector 1109 disposes a rearward end of the needle 102 more proximate to an upper surface of the tubular receptacle 1201 than the lower surface 1200, as the connector 1109 couples to the tubing 106. A glide canal 1128 provides a supported channel at the angle 1202 for guiding the needle along the insertion path 1210 directed to a location below the plane of the bottom surface 1200. The materials defining the base portion 1130 and glide canal 1128 may be thinner than their counterparts in the parallel needle configuration of FIGS. 1 and 2, and therefore may be implemented by stronger materials or alternate shaping to reinforce stress points.

Figure 8:
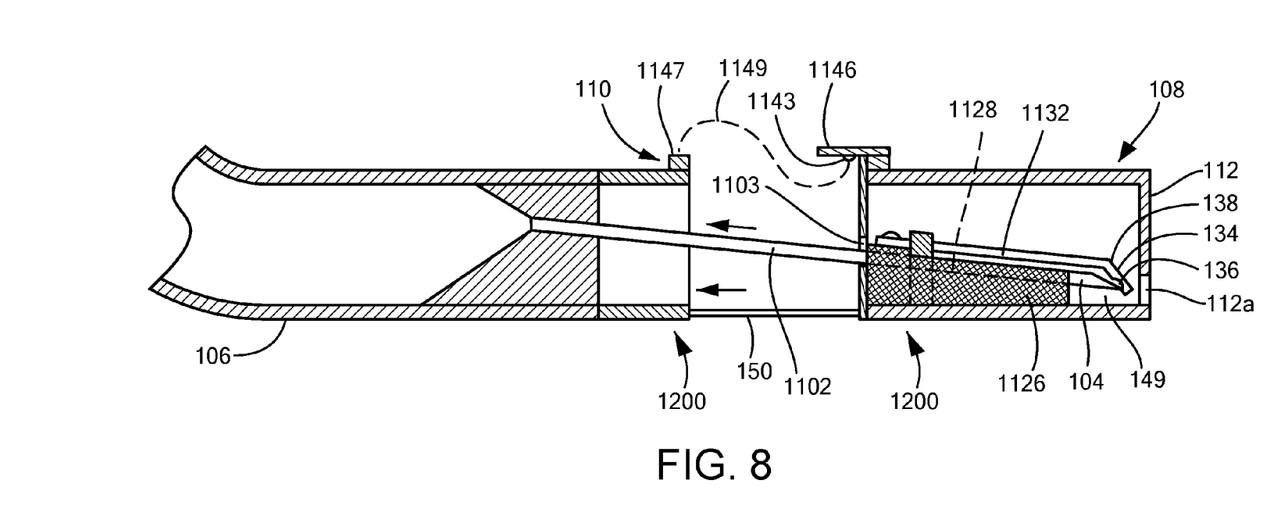
FIG. 8 shows a side view of an angled needle in a safe (retracted) position.

FIG. 8 shows a side view of an angled needle in a safe (retracted) position. Following retraction, as in the parallel configuration, the withdrawn angled needle 1102 recedes inside the enclosure 108 as the front face 134 of the safety cover 132 is drawn in front of the point 104. As in the above configurations, the safety enclosure 108 may include the safety cover 132 defined as a resilient, spring-like strip adjacent and substantially parallel to the needle shaft 1102, such that the face 134 is biased and passes in front of the tip 104 to prevent reemergence of the needle 1102 by impeding outward movement. FIG. 8 shows the angled configuration further including a safety feature responsive to engagement upon retraction of the needle assembly.

The retracted position of FIG. 8 is achieved after releasing a hook portion 146 (FIG. 1), or tab, that engages a protrusion 1147. The release tab 1146 is adapted to engage a protrusion 1147 for coupling the tubular receptacle to the safety enclosure 108, as shown by dotted line 1149, such that the release tab is deformably responsive for disengaging the protrusion for needle retraction by flexing or bending upward to release the protrusion 1147 from a dimple 1143 or recession. In the example of FIGS. 7 and 8, release tab 1146 is disposed on the safety enclosure 108 and is biased to engage the protrusion on the tubular receptacle 1201, however a reverse arrangement may also suffice. Movement for releasing the tubular receptacle for withdrawing the needle 1102 is ideally related or similar such that only a single hand of a user is required. Accordingly, the release tab 1146 is responsive to deformable force at least partially in the direction of an axis of the needle 1102 for allowing single hand disengagement and retraction of the tubular receptacle. The tab 1146, when disposed upwards and forwards toward the front face 112, causes the tab 1146 to displace upwards sufficient to disengage and permit passage of the protrusion 1147 under the tab 1146. Thus, a single deft motion by one hand allows upwards and forward movement on the release tab 1146 to complement the rearward pulling for retracting the needle 1102.

The angled second base portion 1144 defining the angular support includes an upper support at a posterior end of the safety enclosure opposed from the forward end (face), and the upper support slideably secures the elongated shaft at an upper region of the safety enclosure 108, in which the upper region of the enclosure 108 is the region opposed from the base 1200. The angled needle 1102 follows a generally diagonally path through the safety enclosure. An upper surface of the safety enclosure 108 is opposed from the base 1200, such that the upper surface of the tubular receptacle 1201 is substantially parallel with the base 1200 and the needle assembly is supported at the posterior end along an upper half nearer the upper surface than the base.

As with the straight needle configuration, in the angled needle configuration the safety cover 132 has a face portion 134 and an elongated rear portion biasing the face 134 against the elongated shaft in the use position and disposing the face 134 in front of the needle tip 104 when in the safe position. The safe position results from slideably disposing the needle assembly backwards for drawing the needle tip 104 into an interior of the safety enclosure 108, in which the needle is drawn in to the enclosure 108 beyond the front face 112 for disposing the face 134 in front of the needle tip 104 and preventing needle travel back out of the enclosure 108.

Biasing of the safety feature or cover 132 results from a resilient elongated member substantially parallel to the elongated shaft 102, the safety feature fixed at the elongated rear portion and deformable along a length of the elongated rear portion for biasing the face portion 134 against the elongated shaft for disposing the face 134 adjacent to the pointed tip when the tip is retracted rearward of the face portion. A spring-like response from the safety cover disposes the front face 134 in front of the tip 104 once the elongated shaft is drawn backwards sufficiently.

The safe position therefore disposes the needle in concealment within the safety enclosure 108 and causing the needle retained by the safety feature 132. The use position is defined by the needle assembly slideably disposed to extend the needle tip from the safety enclosure and adapted for penetrating the patient dermal surface at the defined angle 1202 when the bottom surface 1200 is flush with the dermal surface. Near flush positioning will still allow angled penetration to mitigate the fulcrum effect ending to draw the needle up and out of the dermal surface from forces on the tube 106 end of the safety enclosure 108.

Figure 9:
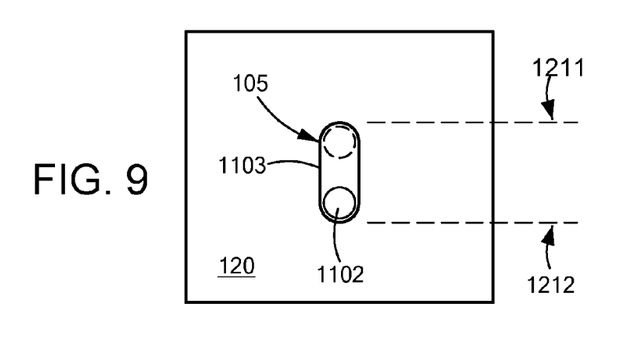
FIG. 9 shows a slot in the retractable portion for accommodating the angled needle.

FIG. 9 shows the slot 1103 in the retractable portion for accommodating the angled needle. Referring to FIGS. 7-9, the oval shaped slot 1103 in the hub portion 110 defines an opening from the uppermost, retracted needle position 1211 to the lowermost (nearest the bottom surface 1200) position 1212 to accommodate the position of the angled needle 1102 and the glide canal 1128 as the hub 110 withdraws the angled needle 1102 and the hub 110 separates from the base portion.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A needle insertion apparatus, comprising:
    a safety enclosure having a needle assembly slideably disposed therein, the needle assembly having a safe position and a use position;
    the needle assembly including a pointed tip, an elongated needle shaft, a tubular receptacle and a cannulated interior for fluidic communication from the needle tip to a fluid conduit attached to the tubular receptacle;
    the safety enclosure adapted to enclose the needle in response to displacement of the needle assembly to the safe position within the safety enclosure; and
    an angular support disposing the needle assembly at an angular orientation relative to a base of the safety enclosure, the base defining a working position of the needle for direct communication with a dermal surface of a patient,
    the angular orientation disposing the needle assembly such that the pointed tip is closer to the base than the tubular receptacle, the needle tip extending below a plane defined by the base when the needle assembly is in the use position; and
    a slot disposed in an interior portion of the safety enclosure, the slot defined by an aperture extending substantially perpendicular to the dermal surface, the needle shaft disposed through the aperture, wherein the needle shaft is located at an upper portion of the slot distal from the dermal surface when the needle assembly is in the use position and wherein the needle shaft is located at a lower portion of the slot when the needle is in the safe position.

2. The apparatus of claim 1 wherein the angular support includes an elevated base angling downward toward a forward end of the safety enclosure, the forward end defined by the pointed tip.

3. The apparatus of claim 2 wherein the base has a thickness defining a height from which the needle tip emerges from the safety enclosure, the needle assembly adapted for slideable insertion into a dermal surface of a patient supporting the safety enclosure.

4. The apparatus of claim 3 wherein the base is adapted for resting substantially flush on the dermal surface of the patient and the needle is adapted to extend below the patient dermal surface in the use position, the base preventing an upward pivotal movement of the needle tip.

5. The apparatus of claim 2 wherein the safety enclosure is elongated along the length substantially parallel to the elongated shaft, the needle assembly slideable along the length of the safety enclosure for retracting the pointed tip inside the safety enclosure as the tubular receptacle is drawn away from the safety enclosure.

6. The apparatus of claim 2 further comprising a safety feature responsive to engagement upon retraction of the needle assembly.

7. The apparatus of claim 6 wherein the angular support includes an upper support at a posterior end of the safety enclosure opposed from the forward end, the upper support slideably securing the elongated shaft at an upper region of the safety enclosure, the upper region opposed from the base.

8. The apparatus of claim 7 wherein the upper region is defined by an upper surface of the safety enclosure opposed from the base, the upper surface substantially parallel with the base and the needle assembly being supported at the posterior end along an upper half nearer the upper surface.

9. The apparatus of claim 8 wherein the safety feature has a face portion and an elongated rear portion, the elongated rear portion biasing the face against the elongated shaft in the use position and disposing the face in front of the needle tip in the safe position.

10. The apparatus of claim 9 wherein the safe position is defined by slideably disposing the needle assembly for drawing the needle tip into an interior of the safety enclosure beyond the face portion for disposing the face in front of the needle tip.

11. The apparatus of claim 9 wherein the safety feature is a resilient elongated member substantially parallel to the elongated shaft, the safety feature fixed at the elongated rear portion and deformable along a length of the elongated rear portion for biasing the face portion against the elongated shaft for disposing the face adjacent to the pointed tip when the tip is retracted rearward of the face portion.

12. The apparatus of claim 2 further comprising a release tab adapted to engage a protrusion for coupling the tubular receptacle to the safety enclosure, the release tab deformably responsive for disengaging the protrusion for needle retraction.

13. The apparatus of claim 12 wherein the release tab is disposed on the safety enclosure and biased to engage the protrusion on the tubular receptacle.

14. The apparatus of claim 13 wherein the release tab is responsive to a deformable force at least partially in the direction of an axis of the needle for allowing single hand disengagement and retraction of the tubular receptacle.

15. The apparatus of claim 1 wherein the safe position disposes the needle in concealment within the safety enclosure, the needle retained by the safety feature, and the use position is defined by the needle assembly slideably disposed to extend the needle tip from the safety enclosure and adapted for penetrating the dermal surface of the patient.

16. The apparatus of claim 1 further comprising at least one tether between the safety enclosure and the tubular receptacle configured to limit travel of the tubular receptacle for preventing complete withdrawal of the needle from the safety enclosure.

17. The apparatus of claim 16 further comprising a pair of tethers on opposed sides of the tubular receptacle.

18. The apparatus of claim 1 wherein the use position corresponds to an extended needle such that the needle shaft occupies the upper portion of the slot and the safe position corresponds to a retracted position such that the needle occupies the lower portion of the slot.

19. The apparatus of claim 18 wherein the slot accommodates downward travel of the needle shaft from the upper portion to the lower portion when the needle assembly transitions from the use position to the safe position as the needle tip is slideably disposed into the safety enclosure during needle retraction from the dermal surface.

* * * * *